(12) United States Patent
West et al.

(10) Patent No.: US 7,465,855 B2
(45) Date of Patent: Dec. 16, 2008

(54) NON-TOXIC ENDOPHYTES, PLANTS INJECTED THEREWITH AND METHODS FOR INJECTING PLANTS

(75) Inventors: Charles P. West, Fayetteville, AR (US); Edgar L. Piper, Springdale, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 236 days.

(21) Appl. No.: 11/068,602

(22) Filed: Feb. 28, 2005

(65) Prior Publication Data

US 2005/0150024 A1    Jul. 7, 2005

Related U.S. Application Data

(63) Continuation-in-part of application No. 10/227,626, filed on Aug. 23, 2002, now abandoned, which is a continuation of application No. 09/639,620, filed on Aug. 15, 2000, now abandoned.

(51) Int. Cl.
*A01H 5/00* (2006.01)
*A01H 5/10* (2006.01)
*A01H 15/00* (2006.01)
*A01N 65/00* (2006.01)
*C12N 1/02* (2006.01)

(52) U.S. Cl. .................. 800/320; 800/295; 424/93.5; 435/911; 435/243; 435/254.1; 435/256.4; 435/41

(58) Field of Classification Search .................. 800/320, 800/295; 424/93.5; 435/911, 243, 254.1, 435/256.4, 41
See application file for complete search history.

(56) References Cited

U.S. PATENT DOCUMENTS

| 6,072,107 A * | 6/2000 | Latch et al. ............... 800/320 |
| 6,111,170 A   | 8/2000 | Latch et al. |
| 6,335,188 B1* | 1/2002 | Schardl et al. ............ 435/193 |
| 6,548,745 B2* | 4/2003 | Hiruma et al. ............. 800/320 |

OTHER PUBLICATIONS

West et al. 1998.Molecular and Cellular Technologies for Forage Improvement, pp. 105-115).*

Latch, GCM and Christensen, MJ. 1985. Artificial infection of grasses with endophytes. Annals of Applied Biology [Ann. Appl. Biol.]. vol. 107, No. 1, pp. 17-24.*
Bouton, J.H. et al., "Infection of tall fescue cultivars with non-toxic endophytes," Proceedings of the 55th Southern Pasture and Forage Crop Improvement Conference, Raleigh, NC (Jun. 12-14, 2000) 6 pages.
Bouton, J.H. et al., "Tall fescue cultivars infected with non-toxic endophytes," American Forage and Grassland Council (Jul. 2000) 125-129.
Butler, J.M. et al., "Forensic DNA typing by capillary electrophoresis using the ABI Prism 310 and 3100 genetic analyzers for STR analysis," Electrophoresis (2004) 25:1397-1412.
Crawford Jr., R.J. et al., "Evaluation of a nontoxic endophyte in 'HiMag' tall fescue," Southwest Missouri Agricultural Research and Education Center, 2001 Research Report, University of Missouri-Columbia, Missouri (2001) 6-7.
Davison, A. et al., "Laboratory temperature variation is a previously unrecognized source of genotyping error during capillary electrophoresis," Molecular Ecology Notes (2003) 3:321-323.
Roberts, C. et al., "Steer performance from tall fescue infected with beneficial endophytes," Missouri Grasslands, Newsletter of the Missouri Forage and Grassland Council (Summer, 2000) 11(2):2 pages.
Schardl, C.L. et al., "Three new species of Epichloe symbiotic with North American grasses," Mycologia (1999) 91 (1):95-107.
West, C.P. et al., "Novel endophyte technology: selection of the fungus," Crop Science Society of America Special Publication No. 26 (1998) 105-115.
Complaint for Damages and Equitable Relief, U.S. District Court for the Western District of Missouri, Joplin Division, *Pennington Seed, Inc: et al. v. Produce Exchange No. 299*, Case No. 04-4194-CV-C-WAK.
First Amended Complaint for Damages and Equitable Relief, U.S. District Court for the Western District of Missouri, Joplin Division, *Pennington Seed, Inc. et al. v. Produce Exchange No. 299*, Case No. 04-4194-CV-C-WAK.
Order Granting University of Arkansas' Motion to Dismiss, U.S. District Court for the Western District of Missouri Central Division, *Pennington Seed Inc. et al. v. Produce Exchange No. 299 et al.*, Case No. 04-4194-CV-C-SOW (Nov. 29, 2004).

(Continued)

*Primary Examiner*—Jon Weber
*Assistant Examiner*—Kailash C Srivastava
(74) *Attorney, Agent, or Firm*—Michael Best & Friedrich LLP

(57) ABSTRACT

A grass with improved environmental stress tolerance and low animal toxicity is disclosed where the grass is infected with an isolated endophyte selected from the groups consisting of USDA-PI no. 269850, Ijoukak, Morocco 92060, Boumalne-de-Dades, Morocco KBG 5921, USDA-PI no. 516560, Oujda, Morocco KBG 5892, and mixtures and combinations thereof. A method for stably infecting the grasses is also disclosed.

9 Claims, No Drawings

OTHER PUBLICATIONS

Order Dismissing Defendants FFR Cooperative, Allied Seed, and Produce Exchange No. 299, U.S. District Court for the Western District of Missouri Central Division, *Pennington Seed Inc. et al.* v. *Produce Exchange No. 299 et al.*, Case No. 04-4194-CV-C-SOW (May, 31, 2005).

Order Granting Defendants Gary C. George, B. Alan Sugg, John A. White, and Charles P. West's Motion to Dismiss, U.S. District Court for the Western District of Missouri Central Division, *Pennington Seed Inc. et al.* v. *Produce Exchange No. 299 et al.*, Case No. 04-4194-CV-C-SOW (Jun. 1, 2005).

Entry of Final Judgment, U.S. District Court for the Western District of Missouri Central Division, *Pennington Seed Inc. et al.* v. *Produce Exchange No. 299 et al.*, Case No. 04-4194-CV-C-SOW (Jun. 1, 2005).

U.S. Court of Appeals Federal Circuit Opinion, *Pennington Seed, Inc. et al.* v. *Produce Exchange No. 299 et al.*, 457 F.3d 1334; 2006 U.S. App. Lexis 20363; 79 U.S.P.Q.2d (BNA) 1777.

* cited by examiner

NON-TOXIC ENDOPHYTES, PLANTS INJECTED THEREWITH AND METHODS FOR INJECTING PLANTS

RELATE APPLICATIONS

This application is a Continuation-in-Part of U.S. patent application Ser. No. 10/227,626 filed Aug. 23, 2002, now abandonded, which is a continuation of U.S. patent application Ser. No. 09/639,620 filed Aug. 15, 2000, now abandonded. The new matter added relates to micro-satellite analysis of the disclosed endophytes according to the analysis procedure set forth in U.S. Pat. Nos. 6,111,170 and 6,072,107 to evidence a clear distinction between the endophytes of this invention and the endophytes of U.S. Pat. Nos. 6,111,170 and 6,072,107.

BACKGROUND OF THE INVENTION

1. Field of the Invention

This invention relates to endophytic fungi, to plants infected with the fungi, to a method of introducing endophytic fungi into the plants and to methods for planting the infected plants, where the endophytic fungi improve the plant's tolerance to environmental stresses and reduce or eliminate the production of agents that are toxic to livestock or other grazing animals.

More particularly, this invention relates to endophytic fungi of the genus *Neotyphodium* that when artificially introduced into a plant improve the plant's tolerance to environmental stresses while rendering the plant substantially non-toxic to livestock or other grazing animals, to plants infected or inoculated with the fungi, to a method of introducing the endophytic fungi into plants and to methods for replacing existing forage plant species and varieties with the new drought tolerant, non-toxic endophyte infected varieties.

2. Description of the Related Art

Grasses, tall fescues and other related species in the genera *Festuca, Lolium* and their hybrids are often a food source for grazing animals. Such vegetation are typically not sufficiently tolerant to environmental stresses such as drought, drought and excess heat or other forms of water or heat stress to be used in many arid or semi-arid or hot climes. Typically, these grasses, fescues or other related species occur in the wild, and these plants occur, with high frequency, in nature infected with filamentous internal fungi, i.e., endophytes. These endophytes grow particularly well in the gaps between cells, i.e., the intercellular spaces. These endophytes, or symbiotic filamentous fungi, do not adversely affect the host plant and can provide the plant with useful substances, improve the plant's tolerance of environmental stresses, and deter feeding on the plants by mammals, insects, and nematodes.

Enhancement by endophytes are known to impart the following properties to their host plants: insect resistance (Siegel et al, 1987 *Ann. Rev. Phytopathol.* 25:293-315); disease resistance (Gwinn and Gavin, 1992,*Plant Disease* 76:911-914); environmental stress (drought, etc.) resistance (Arachevalta et al, 1989 *Agron J.* 81:83-90), and growth enhancement (Latch et al, 1985, *N.Z.J Agric. Res.* 28:165-168). Moreover, endophyte-infected perennial ryegrasses have improved insect resistance due to certain alkaloids produced by the endophyte.

Although certain endophytes have been identified that impart useful traits to their host plants, it would represent an advancement in the art to have available to industries that utilize grasses, fescues and other similar plant life, endophytes that stably infect such plants and impart good tolerance to environmental stresses and reduced production of substances toxic to livestock or other grazing animals.

SUMMARY OF THE INVENTION

The present invention provides endophytes capable of stably infecting grasses, fescues or related vegetation that produce infected plants being non-toxic or having reduced toxicity to livestock or grazing animals and improved tolerance to environmental stresses. The endophytes are preferably from the genus *Neotyphodium* and especially endophytes selected from the group consisting of USDA-PI no. 269850 (deposited as strain UARK 3 having deposit number PTA-8827); Ijoukak, Morocco 92060 (deposited as strain UARK4 having deposit number PTA-6499); Oujda, Morocco KBG 5892; (deposited as strain UARK 9 having deposit number PTA-8829); Boumalne-de-Dades, Morocco KBG 5921(deposited as strain UARK 11 having deposit number PTA-8828); USDA-PI no. 516560, mixtures and combinations thereof. The infected plants are preferably from the genera *Festuca, Lolium* and their hybrids. Preferred plants are tall fescue grasses, *Festuca arundinacea* Schreb (syn. *Lolium arundinaceum*).

The present invention provides a grass, fescue or related plant artificially infected with an endophyte of this invention, where the endophyte imparts to the plant improved tolerance to environmental stresses and reduced, low or no toxicity to livestock or other grazing animals. The endophytes are preferably from the genus *Neotyphodium* and especially endophytes selected from the groups consisting of USDA-PI no. 269850 (deposited as strain UARK 3 having deposit number PTA-8827); Ijoukak, Morocco 92060 (deposited as strain UARK4 having deposit number PTA-6499, Oujda, Morocco KBG 5892 (deposited as strain UARK 9 having deposit number PTA-8829); Boumalne-de-Dades, Morocco KBG 5921 (deposited as strain UARK 11 having deposit number PTA-8828); USDA-PI no. 516560, mixtures and combinations thereof. The infected plants are preferably from the genera *Festuca, Lolium* and *Festuca ×Lolium* hybrids and *Poa*.

This invention also relates to methods for artificially introducing endophytes of this invention into uninfected plants including the step of cultivating an isolated endophyte, inoculating a grass with the isolated endophyte, cultivating the inoculated grass and testing the inoculated grass for desired attributes such as alkaloid production using high performance liquid and gas chromatography, where the introduction is stable (the endophytic infection will propagate through seed to subsequent generations) and produces infected plants with improved tolerance to environmental stresses and low toxicity to livestock and other grazing animals. The method can also include rejecting those endophytes that produce unacceptable levels of alkaloids. The method can further include seeding the inoculated grass to insure that the offspring carry the endophyte and optionally rejecting those endophytes that fail to be stably transmitted to seeds.

DETAILED DESCRIPTION OF THE INVENTION

The inventors have found, identified, isolated and cultivated a series of endophytic fungi or endophytes that are capable of stable inoculation into host plants imparting the host plants improved tolerance to environmental stresses including drought tolerance. The cultivated endophytes also either display low toxicity or are non-toxic to livestock and other grazing animals. The isolated endophytes are USDA-PI no. 269850 (deposited as strain UARK 3 having deposit number PTA-8827); Ijoukak, Morocco 92060 (deposited as strain UARK4 having deposite number PTA-6499); Oujda, Morocco KBG 5892(deposited as strain UARK 9 having deposit number PTA-8829); Boumalne-de-Dades, Morocco KBG 5921(deposited as strain UARK 11 having deposit number PTA-8828); USDA-PI no. 516560, mixtures and combinations thereof. The preferred endophytes are PTA-6499, PTA-8827, PTA-8828, PTA-8829, mixtures and combinations thereof. Each of the indicated endophytes has been deposited with the American Type Culture Collection (ATCC). Deposit number PTA-6499 was deposited on Jan. 5, 2005. The strains deposited as PTA-8827, PTA-8828 and PTA-8829 were deposited on Dec. 5, 2007. All of the indicated strains were deposited under the terms of the Budapest Treaty.

The inventors developed an approach to identify beneficial endophytes that naturally do not produce ergot alkaloids and improved host persistence under environmental stresses such as drought and heavy grazing pressure. The methodology comprises collecting native or existing tall fescue plants, identifying and isolating endophytes found in the native plants. The endophytes were then transferred into improved cultivars, and evaluated for continued lack of ergot alkaloid production, which causes fescue toxicosis in animals. This involves the selection of endophytes that possess a desirable profile of alkaloids that can be expressed in any tall fescue plants, and their seed offspring, infected with these endophyte.

The strains of endophyte identified in this invention can be stably introduced into cultivars of tall fescue or other native plants to enhance their persistence when used for forage and ground cover (soil conservation, turf), yet have the characteristics of low or no toxicity to grazing animals.

The present invention broadly relates to a set of endophytic fungi, endophytes, including USDA-PI no.269850 (deposited as strain UARK 3 having deposit number PTA-8827); Ijoukak, Morocco 92060 (deposited as Strain UARK 4 having deposit number PTA-6499); Oujda, Morocco KBG 5892 (deposited as strain UARK 9 having deposit number PTA-8829); Boumalne-de-Dades, Morocco KBG 5921(deposited as strain UARK 11 having deposit number PTA-8828); USDA-PI no. 516560, mixtures and combinations thereof, which impart to their host plants improved tolerance to environmental stresses, such as drought and heat, yet are substantially non-toxic to livestock or other grazing animals. The endophytes of this invention are particularly well suited for use in grasses, fescues or other similar vegetation. These plants generally form a significant part of the food stuff for livestock or other grazing animals, especially in regions of the world characterized by an extended hot season where tolerance to heat and drought are desirable attributes. The endophytes of this invention are also well suited for use in grasses used in turf for which the seed production involves collecting the crop residue and using it as a food stuff for livestock or other grazing animals. The turf grasses can be associated with residential lawns or commercial lawns such as golf courses. Thus, the endophytes of the present invention can improve heat and drought tolerance of useful grasses or other plants; while rendering them substantially non-toxic to livestock. Livestock toxicity is a major problem with most naturally occurring *Neotyphodium* endophytes because the endophytes generally produce toxic secondary plant metabolites such as alkaloids or other toxic substances.

The present invention also broadly relates to plants including grasses, fescues or other similar plants capable of stable infection by endophytes that have been stably infected by one or more of the endophytes of this invention and to their use as a food stuff for livestock, golf courses, lawns, natural turf stadiums and arenas, or other similar facilities.

The present invention further broadly relates to methods for endophyte inoculation and testing for stable infection, which involves cultivating an isolated endophyte, inoculating a grass with the isolated endophyte, cultivating the inoculated grass and testing the inoculated grass for desired attributes such as alkaloid production using a chromatographic separation technique such as high performance liquid and gas chromatography. The method also includes rejecting those endophytes that produce unacceptable levels of alkaloids. The method also includes seeding the inoculated grass to insure that the offspring carry the endophyte and optionally rejecting those endophytes that fail to be stably transmitted to seeds.

Suitable plants into which these endophytes can be introduced include, without limitation, any plant capable of being infected in a stable manner by endophytic fungi such as grasses including, but not limited to, the genera *Agropyron, Agrostis, Andropogon, Anthoxanthum, Arrhenatherum, Avena, Brachypodium, Bromus, Chloris, Cynodon, Dactylis, Elymus, Eragrostis, Elytrigia, Festuca, Glyceria, Hierochloe, Hordeum, Lolium, Leymus, Oryza, Panicum, Paspalum, Phalaris, Phleum, Poa, Secale, Setaria, Sorghum, Stipa, Triticum, Zea, Zoysia* and their hybrids. Preferred grasses include grasses from the genera *Festuca, Lolium* and *Festuca×Lolium* hybrids and *Poa*.

Procedure

There were more than one source of the tall fescue germplasm that provided beneficial endophytes. The first source was the existing germplasm (accessions) at the USDA Plant Introduction Station at Pullman, Wash. Samples of tall fescue seeds were obtained and screened for endophyte presence by soaking 20 seeds in 5% NaOH for 16 hours, rinsed with deionized water, dehulled, stained with 0.5% rose bengal, and then squashed with a cover slip. Each slide was examined through a microscope.

For those accessions that contained endophyte in the seed, other seed was planted in soil in a greenhouse and grown up for at least 8 weeks. Leaf sheath bases were excised and microscopically analyzed for endophyte mycelia. This identified accessions which contained live endophyte. Six plants of each accession that contained live endophyte were transplanted to pots, clipped to a 5 cm stubble, then regrown for 3 to 4 weeks depending on the accession. Plant leaves were clipped again, the leaves were lyophilized, ground through a 1 mm screen, then analyzed for ergovaline production by high performance liquid chromatography (HPLC) for ergovaline production (method of Rottinghaus et al., 1991, detection limit of 50 ng/g, later modified by Moubarak et al., 1996 to attain detection limit of 10 ng/g).

The criterion for selecting accessions for further study and endophyte isolation was the complete lack of chromatogram peaks that were suspected to represent any ergopeptine alkaloids. Ergovaline was chosen as the marker livestock toxin because it is the predominant ergopeptine alkaloid present in endophyte-infected tall fescue. Within an accession, only one of the six (6) plants grown was saved as a host containing a potentially beneficial endophyte. Other plants in the accession lacking ergovaline were assumed to possess the same strain of endophyte as the one selected, therefore they were discarded. Two strains (strains 3 and 12) originating from the Plant Introduction source eventually passed subsequent tests of consistently maintaining the absence of ergopeptine alkaloids when transferred to new hosts.

Collections of tall fescue accessions were made to acquire freshly harvested seed with viable endophytes in Morocco.

Seed of five accessions was obtained and plants were grown in a greenhouse. Leaf tissue was analyzed for ergovaline production. Four of the five accessions were found to contain no ergovaline or related peaks (strains 8, 9, 10, and 11).

Some live plants were collected as well as seed. The live plants were grown in a growth chamber to produce enough leaf mass to analyze for ergovaline by HPLC. One plant was found to contain an endophyte which produced no ergovaline (strain 4).

Seeds from other collected tall fescue were grown in a greenhouse as seedlings, then transplanted to seed-increase plots. Plant samples were analyzed for ergovaline, and seeds were harvested from those accessions in which no ergovaline was detected on HPLC. The remaining accessions were grown in the field for seed increase. Seed was subsequently harvested. The next generation of seeds was grown out in a greenhouse and the plants were analyzed for ergovaline by HPLC. The ergovaline screening procedure resulted in selection of endophytes that lacked the ability to produce ergopeptine alkaloids in their native host plants.

The next step involved isolating the selected endophytes from the native hosts and inoculating them into useful tall fescue cultivars for forage use. The expression of ergovaline was again analyzed to determine 1) their compatibility with a new host, and 2) whether the lack of ergopeptine alkaloids was a stable expression in a forage cultivar.

Endophytes were isolated from the selected plants by excising leaf sheath tissue. Leaf sheaths were surface-disinfected with 50% household bleach solution for 20 minutes and rinsed in sterile deionized water three times. Leaf sheaths were then sliced into 2 mm cross-sections and plated on potato dextrose agar. Plates were incubated at 20° C. in the dark until mycelia emerged. Emerging mycelia were subcultured to potato dextrose agar plates to increase mycelial mass. Mycelial colonies were excised from the agar, placed in tubes of sterile deionized water, and ground with a homogenizer. Plates of proline glutamic acid medium were covered with sterile cellophane film. Mycelial slurry was spread on the cellophane film and incubated at 20° C. in the dark for 5 days.

Endophyte-free seedlings of the tall fescue cultivar HiMag were inoculated with the selected isolates by the seedling-stab technique (See Latch and Christensen, 1985; Siegel and Bush, 1994). The technique involved germinating surface-sterilized seed on 2% water agar for 5 days in the dark, stabbing a hole with an insect pin just above the coleoptilar node, and inserting a small mass of mycelia into the opening using the insect pin and forceps. The seedlings were placed in an incubator at 20° C. in the dark for one week, then were transplanted to small pots under laboratory bench lights. Gradually the surviving seedlings were hardened to normal greenhouse conditions and checked for endophyte infection before transplanting to the field.

A new seed crop was produced the following year. Only seeds of those plants which were still infected with the inoculated endophytes were harvested. The percentage of seeds containing endophyte that was transferred from the mother plant was determined by staining a subsample of seeds with aniline blue and examining under a microscope for mycelia. Those strains which showed 100% of seeds infected were deemed to be compatible associations with the selected endophytes.

Seeds of cultivar HiMag infected with strains 4, 9, 10, 11, and 12, and of endophyte-free HiMag were planted in the field. The field conditions were typical for south-central Oklahoma and were a sandy soil, very susceptible to drought stress in the summer. The summer growing conditions were very dry and hot. The number of surviving plants of each entry was counted at the end of the summer to ascertain survival rate under drought stress.

Results

The strains of endophytes that survived the initial screening process are tabulated in Table 1.

TABLE 1

Endophyte Strain Number and Source

| Strain no. | Source |
| --- | --- |
| 3 | USDA-PI no. 269850 |
| 4 | Ijoukak, Morocco |
| 8 | Ouarzazate, Morocco |
| 9 | Oujda, Morocco |
| 10 | El-Kelaa-des-Mgouna, Morocco |
| 11 | Boumalne-de-Dades, Morocco |
| 12 | USDA-PI no. 516560 |

Microsatellite Analysis of four endophytes of this invention are reported below, where the microsatellite analyses was performed in accordance with the procedure set forth in U.S. Pat. Nos. 6,111,170 and 6,072,107:

TABLE 2

Microsatellite Analysis of Endophytes

| Locus | USDA-PI No. 269850 | Ijoukak, Morocco 92060 | USDA-PI No. 516560 and Oujda, Morocco KBG 5892 | Boumalne-de-Dades, Morocco KBG 5921 |
| --- | --- | --- | --- | --- |
| B4 | 119.49 | 102.98 | 102.99 | 102.92 |
| B6 | 173.45 | 194.51 | 194.62 | 197.52 |
| B9 | 273.27 | 272.81 | 273.85 | 272.85 |
| B10 | 201.93 | 164.17, 166.91 | 164.09, 184.17 | 164.27, 201.85 |
| B11 | 129.63 | 166.54, 193.67 | 166.54, 197.69 | 170.25, 193.73 |

The data support two new sub-classes of Neotyphodium endophytes.

The number and strain of the endophytes that survived the severe drought conditions are shown in Table 3.

TABLE 3

Number of surviving HiMag tall fescue plants at Ardmore, OK at the end of a severe drought.

| Strain number[1] | No. of surviving plants[2] |
| --- | --- |
| Control | 0[a] |
| 4 | 9[b] |
| 9 | 10[b] |
| 10 | 21[b] |
| 11 | 15[b] |
| 12 | 6[b] |

[1]Control was HiMag tall fescue without any endophyte. The others contained endophyte of the strains listed below.
[2]Means of three replications. Different letters in superscript indicate significant differences at $P < 0.05$.

Grazing trials to show nontoxic effect on cattle at Southwest Center MO. and Fayetteville Ark.

TABLE 4

Animal response data from Southwest Center, Missouri, 1999

| | Fescue/Endophyte Treatment[1] | | |
|---|---|---|---|
| Measurements | KY+ | HiMag 4 | HiMag– |
| Daily weight gain (kg) | 0.33[a] | 0.57[b] | 0.59[b] |
| Hair score (1 = smooth, 5 = rough) | 3.67[a] | 2.44[b] | 2.17[b] |
| Respiration rate (per min.) | 114.8[a] | 90.4[b] | 77.4[b] |
| Rectal temperature (° C.) | 41.0[a] | 40.4[b] | 39.8[b] |
| Serum prolactin (ng/mL) | 9.6[a] | 50.8[b] | 90.4[c] |

[1] KY + = 'Kentucky-31' tall fescue infected with native, toxic endophyte.
HiMag 4 = 'HiMag' tall fescue infected with endophyte strain 4.
HiMag – = 'HiMag' tall fescue infected with no endophyte.
Data are means of three replications. Different letters in superscript indicate significant differences at $P < 0.05$.

TABLE 5

Animal response data from University of Arkansas, Fayetteville, 1999

| | Fescue/Endophyte Treatment[1] | | | |
|---|---|---|---|---|
| Measurements | KY+ | HiMag 4 | HiMag 9 | HiMag– |
| Daily weight gain (kg) | 0.47[a] | 0.70[a] | 0.75[a] | 0.72[a] |
| Respiration rate (per min.) | 81.7[a] | 63.7[b] | 63.4[b] | 59.4[b] |
| Rectal temperature (° C.) | 39.8[a] | 39.7[b] | 39.6[b] | 39.2[b] |
| Serum prolactin (ng/mL) | 10.2[a] | 129.5[b] | 91.9[ab] | 111.7[b] |

[1] Same treatments as above with addition of 'HiMag' 9 = 'HiMag' tall fescue infected with endophyte strain 9.
Data are means of two replications. Different letters in superscript indicate significant differences at $P < 0.05$.

The results in animal grazing trials indicate that tall fescue containing endophytes 4 and 9 do not produce symptoms of toxicosis in cattle. The other endophyte strains covered by this patent also do not contain ergopeptine alkaloids, and therefore would be expected to perform the same as for strains 4 and 9.

REFERENCES

1. Latch, G. C. M., and M. J. Christensen. 1985. Artificial infection of grasses with endophytes. Ann. Appl. Bot. 107: 17-24.
2. Moubarak A. S., E. L. Piper, Z. B. Johnson, and M. Flieger. 1996. HPLC Method for detection of ergotamine, ergosine, and ergine after intravenous injection of a single dose. J. Agric. Food Chem. 44:146-148.
3. Rottinghaus, G. E., G. B. Garner, C. N. Cornell, and J. L. Ellis. 1991. HPLC method for quantitating ergovaline in endophyte-infested tall fescue: Seasonal variation of ergovaline levels in stems with leaf sheaths, leaf blades, and seed heads. J. Agric. Food Chem. 39:112-115.
4. Siegel, M. R., and L. P. Bush. 1994. Importance of endophytes in forage grasses, a statement of problems and selection of endophytes. p. 135-150. In C. W. Bacon and J. F. White, Jr. (ed.) Biotechnology of endophytic fungi of grasses. CRC Press, Boca Raton, Fla.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A plant from the genus *Lolium* or *Festuca* or their hybrids, wherein the plant is artificially and stably infected with an endophyte having an ATCC accession number selected from the group consisting of PTA-6499, PTA-8827, PTA-8828, PTA-8829, and mixtures and combinations thereof, and wherein the endophytes have the microsatellite loci as indicated in Table 2.

2. The endophyte-infected plant of claim 1, wherein the endophyte comprises PTA-8827.

3. The endophyte-infected plant of claim 1, wherein the endophyte comprises PTA-8828.

4. The endophyte-infected plant of claim 1, wherein the endophyte comprises PTA-8829.

5. The endophyte-infected plant of claim 1, wherein the plant is a species of *Festuca*.

6. The endophyte-infected plant of claim 1, wherein the plant is a species of *Lolium*.

7. An endophyte-infected seed from the endophyte-infected plant of claim 1.

8. Endophyte-infected progeny of the endophyte-infected plant of claim 1.

9. A plant from the genus *Lolium* or *Festuca* or their hybrids, wherein the plant is artificially and stably infected with an endophyte having ATCC accession number PTA-6499 and wherein the strain comprises the microsatellite loci as indicated in Table 2.

* * * * *